(12) United States Patent
Tamura et al.

(10) Patent No.: US 6,994,965 B2
(45) Date of Patent: Feb. 7, 2006

(54) METHOD FOR DISPLAYING RESULTS OF HYBRIDIZATION EXPERIMENT

(75) Inventors: Takuro Tamura, Kanagawa (JP); Noriyuki Yamamoto, Kanagawa (JP); Nobuaki Suzuki, Kanagawa (JP); Katsuya Mizuno, Kanagawa (JP)

(73) Assignee: Hitachi Software Engineering Co., Ltd., Kanagawa (JP)

(*) Notice: Subject to any disclaimer, the term of this patent is extended or adjusted under 35 U.S.C. 154(b) by 315 days.

(21) Appl. No.: 09/808,407

(22) Filed: Mar. 14, 2001

(65) Prior Publication Data

US 2002/0021299 A1  Feb. 21, 2002

(30) Foreign Application Priority Data

Mar. 14, 2000  (JP) ............................. 2000-070915

(51) Int. Cl.
  *C12Q 1/68*  (2006.01)
  *C07H 21/04*  (2006.01)

(52) U.S. Cl. .................. 435/6; 536/23.1; 536/24.3; 536/24.31

(58) Field of Classification Search .............. 435/6, 435/7.1, 91.1, 91.2, 287.2, 288.4; 536/22.1, 536/23.1, 243.33, 24.32, 24.3, 24.33; 345/440; 382/129

See application file for complete search history.

(56) References Cited

U.S. PATENT DOCUMENTS 6,344,316 B1 *  2/2002  Lockhart et al. ............... 435/6
6,528,264 B1 *  3/2003  Pal et al. ....................... 435/6

OTHER PUBLICATIONS

Lockhart et al Nature Biotechnology vol. 14 pp. 1675-1680 1996.*
Schena et al Science vol. 270 pp 467-470 1995.*
Lockhart et al. Expression Monitoring by hybridization to high density oligonucleotide arrays. Nature Biotechnology, vol. 14, pp. 1675-1680, Dec. 1996.*
Eisen et al. Cluster Analysis and display of genome-wide expression patterns, PNAS. vol. 95, pp. 14863-14868, Dec. 1998.*
Tatusova et al. BLAST 2 sequences, a novel tool for comparing protein and nucleotide sequences, FEMS Microbiology letters vol. 174, pp. 247-250, 1999.*
Cheung et al., "Making and Reading Microarrays", Nature Genetics Supplement, vol. 21 (Jan. 1999), pp. 15-19.
Lipshutz et al., "High Density Synthetic Oligonucleotide Arrays", Nature Genetics Supplement, vol. 21 (Jan. 1999), pp. 20-24.
Smith et al., "Identification of Common Molecular Subsequences", J. Mol. Biol., vol. 147 (1981), pp. 195-197.
Altschul et al., "Gapped BLAST and PSI-Blast: A New Generation of Protein Database Search Programs", Nucleic Acids Research, vol. 25, No. 17 (1997), pp. 3389-3402.
Eisen et al., "Cluster Analysis and Display of Genome-Wide Expression Patterns", Proc. Natl, Acad. Sci., vol. 95 (Dec. 1998), pp. 14863-14868.
European Search Report dated Jan. 5, 2005.
S. Chu et al., "The Transcriptional Program of Sporulation in Budding Yeast", Science, vol. 282 (Oct. 23, 1998), pp. 699-705.
Paul T. Spellman et al., "Comprehensive Identification of Cell Cycle-Regulated Genes of the Yeast Saccharomyces Cerevisiae by Microarray Hybridization", Molecular Biology of the Cell, vol. 9 (Dec. 1998), pp. 3273-3297.
Andreas D. Baxevanis, Editor, "Bioinformatics—A Practical Guide to the Analysis of Genes and Proteins", John Wiley & Sons, Inc. (1998), 3 pages.
Amir Ben-Dor et al., "Clustering Gene Expression Patterns", Hewlett-Packard Company (1998), cover page and pp. 1-12.

* cited by examiner

*Primary Examiner*—Kenneth R. Horlick
*Assistant Examiner*—Cynthia Wilder
(74) *Attorney, Agent, or Firm*—Reed Smith LLP; Stanley P. Fisher, Esq.; Juan Carlos A. Marquez, Esq.

(57) ABSTRACT

In a method for verifying the accuracy of hybridization experiments in which a plurality of probe biopolymers are hybridized to sample biopolymers, information concerning the hybridization level for each of the probe biopolymers obtained from the hybridization experiment is displayed together with similarity scores representing the similarities between base sequences of the respective probe biopolymers.

9 Claims, 10 Drawing Sheets

EXAMPLE OF DATA STRUCTURE

FIG.4

EXAMPLE OF BIOCHIP DATA

300

| BIOCHIP ID | BIOCHIP NAME | BIOCHIP DEFINITION INFORMATION | BIOCHIP EXPERIMENT INFORMATION |
|---|---|---|---|
| 1 | Chip 1 | Definition about Chip 1 | Sample from the Stage A (1D) |
| 2 | Chip 2 | Definition about Chip 2 | Sample from the Stage B (3D) |
| 3 | Chip 3 | Definition about Probe 3 | Sample from the Stage C (1W) |
| : | : | : | |
| n | Chip n | Definition about Chip n | not used. |

FIG.5

EXAMPLE OF DNA PROBE DATA

301

| DNA PROBE ID | DNA PROBE NAME | DNA PROBE DEFINITION INFORMATION | DNA PROBE SEQUENCE |
|---|---|---|---|
| 1 | Probe1 | Definition about Probe 1 | ACGGGACGTTCCCTCGGAGG |
| 2 | Probe2 | Definition about Probe 2 | ACGGGACGTTCCCCCGGAGG |
| 3 | Probe3 | Definition about Probe 3 | TTTGGACGTTCCAATAGAGG |
| 4 | Probe4 | Definition about Probe 4 | TTTGGACGTTCCAATAGGGG |
| 5 | Probe5 | Definition about Probe 5 | TTGGGACGTTCCAATAGGAG |
| : | : | : | : |
| m | Probe m | Definition about Probe n | TTGGGACGTTCCAATAGGAG |

FIG.6

EXAMPLE OF HYBRIDIZATION-LEVEL DATA

302a

| BIOCHIP ID | DNA PROBE ID | HYBRIDIZATION LEVEL | SPOT IMAGE |
|---|---|---|---|
| 1 | 1 | 31,916 | |
| 1 | 2 | 224 | |
| 1 | 3 | 41.231 | |
| 1 | 4 | 24,107 | |
| 1 | 5 | 9,607 | |
| : | : | : | |
| 1 | m | 9,753 | |

302b

| BIOCHIP ID | DNA PROBE ID | HYBRIDIZATION LEVEL | SPOT IMAGE |
|---|---|---|---|
| 2 | 1 | 43,416 | |
| 2 | 2 | 41,224 | |
| 2 | 3 | 2,107 | |
| 2 | 4 | 25,307 | |
| 2 | 5 | 1,807 | |
| : | : | : | |
| 2 | m | 853 | |

302c

| BIOCHIP ID | DNA PROBE ID | HYBRIDIZATION LEVEL | SPOT IMAGE |
|---|---|---|---|
| 3 | 1 | 21,916 | |
| 3 | 2 | 11,224 | |
| 3 | 3 | 10,007 | |
| 3 | 4 | 21,107 | |
| 3 | 5 | 1,507 | |
| : | : | : | |
| 3 | m | 5,753 | |

EXAMPLE OF CALCULATED SIMILARITY SCORES

| Target \ Key | Probe1 | Probe2 | Probe3 | Probe4 | Probe5 |
|---|---|---|---|---|---|
| Probe1 | 80 | 76 | 40 | 56 | 44 |
| Probe2 | 76 | 80 | 44 | 52 | 44 |
| Probe3 | 40 | 44 | 80 | 36 | 52 |
| Probe4 | 56 | 52 | 36 | 80 | 48 |
| Probe5 | 44 | 44 | 52 | 48 | 80 |

FIG.8

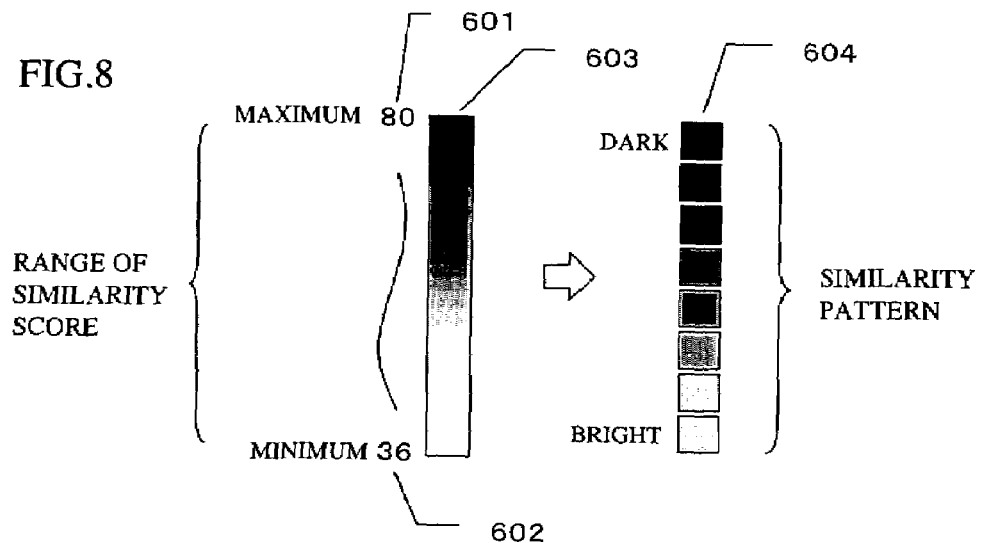

FIG.9

| DNA PROBE ID | DNA PROBE NAME | DNA PROBE DEFINITION INFORMATION | DNA PROBE SEQUENCE | SIMILARITY SCORE | SIMILARITY PATTERN |
|---|---|---|---|---|---|
| 1 | Probe1 | Definition about Probe 1 | ACGGGACGTTCCCTCGGAGG | 80 | |
| 2 | Probe2 | Definition about Probe 2 | ACGGGACGTTCCCCCGGAGG | 76 | |
| 3 | Probe3 | Definition about Probe 3 | TTTGGACGTTCCAATAGAGG | 40 | |
| 4 | Probe4 | Definition about Probe 4 | TTTGGACGTTCCAATAGGGG | 56 | |
| 5 | Probe5 | Definition about Probe 5 | TTGGGACGTTCCAATAGGAG | 44 | |
| : | : | : | : | | |
| m | Probe m | Definition about Probe n | TTGGGACGTTCCAATAG... | nn | |

* Similarity score is a similarity score of each of the DNA probes with respect to the DNA probe:ID 1.

FIG.10

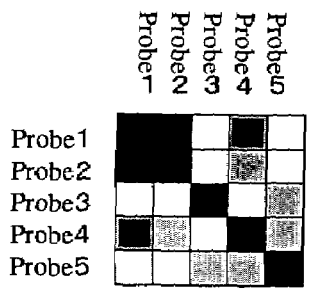

EXAMPLE OF GENERATING HYBRIDIZATION-LEVEL PATTERN

EXAMPLE OF CONVERTING HYBRIDIZATION-LEVEL PATTERN

METHOD FOR DISPLAYING RESULTS OF HYBRIDIZATION EXPERIMENT

This application claims priority to Japanese Application Serial No. 2000-70915, filed Mar. 14, 2000.

BACKGROUND OF THE INVENTION

1. Field of the Invention

The present invention relates to a method for displaying results of hybridization experiments in which a biochip is used to hybridize a sample biopolymer with a probe biopolymer with a known sequence.

2. Detailed Description of the Prior Art

Biochips, also known as DNA micro arrays, have been developed to simultaneously quantify various biopolymer species, such as DNA sequences, that are present in a sample in different volumes. The technology is overviewed in Vivian G. Cheung et al., "Making and reading microarrays," *Nature Genetics Supplement*, vol. 21, January 1999. In a typical biochip technique, different probe biopolymers, for example, DNA molecules, are immobilized on a surface of a support such as glass slides and, through hybridization, selectively bind to different labeled biopolymers, for example, DNA sequences, in a sample. Specific sample biopolymers can be quantified based on the amounts of markers that have been selectively coupled to the probe biopolymers via sample biopolymers hybridized to the probe biopolymers. This principle makes it possible to quantify many different sample biopolymers at a time by immobilizing many different probe biopolymers on the same support.

In order for two DNA sequences to hybridize, the two sequences need to have base sequences complementary, or nearly complementary, to one another. When hybridized, the complementary strands have a high binding energy and are stable at a certain temperature. This binding energy varies depending on the length and base composition (GC content) of the strand. Two hybridized strands with partially non-complementary sequences can also have a sufficiently high binding energy when they contain complementary regions of sufficient lengths. This means that there is a chance that sample DNA molecules of the same type bind to two different types of DNA probes that are very similar to one another. It is known that the likelihood that this unintended hybridization (miss-hybridization) occurs varies depending on the conditions of hybridization experiments.

A type of biochips that uses synthetic short DNA strands as DNA probes is known (oligonucleotide array). In this type of biochips, DNA molecules with sequences similar to respective subject DNA probes are synthesized and used to serve as DNA probes for comparison so as to determine if the hybridized sample DNA is the intended sequence as the target of the subject DNA probe. This technique is reviewed by Robert J. Lipshutz et al (Robert J. Lipshutz et al.: High density synthetic oligonucleotide arrays, Nature Genetics Supplement, Vol. 21, January 1999).

However, in biochips that use longer DNA molecules, such as cDNA, as a probe biopolymer, no effective technique is known that can evaluate the results of hybridization using DNA sequence data.

The Smith-Waterman method is a known technique for searching for regions with highest homology between two different DNA sequences (Smith, T. F. and Waterman, M. S.: J. Mol. Biol. 147, 195–197, 1981). Also, methods are known such as BLAST that allow for a fast search for a target sequence having a high homology with a DNA sequence of interest (key sequence) among many different DNA sequences (targets) (Altschul et al., Nucleic Acids Res., 25, 3389–3402, 1997). Many other algorithms have been developed for the same purpose. In these approaches, the degrees of homology between two DNA sequences are expressed by indices such as "homology score," which is based on the scores used in the search for high homology regions between the two DNA sequences, or by "matching rate," which is based on the proportion of the complementary DNA portions in the region (these indices, each representing the degree of homology, are collectively referred to as "similarity score," hereinafter.).

In a technique widely used for data analysis of biochip experiments, subject DNA proves are statistically classified (i.e., clustered) based on the changes in levels of hybridization in a plurality of biochips. In the expression analysis for yeast conducted by P. Brown's group of the Stanford University, a DNA sample was prepared at each stage of cell development in a time-sequential manner and the samples were each hybridized to separate biochips. Types and the amounts of DNA sequences present in the DNA samples were determined for each stage. The DNA sequences (DNA probes) were then clustered based on the changes in amounts at each stage (Michel B. Eisen et al.: Cluster analysis and display of genome-wide expression patterns: Proc. Natl. Acad. Sci. (1998) Dec. 8, 1995 (25), 14863-8). The results are displayed in a tree diagram obtained from the clustering that indicates the order of clusters in the DNA sequence and the distances between the clusters. The results also include information about the DNA sequences (e.g., name, definitions, or the like) and hybridization patterns indicating the levels of hybridization for each DNA sequence on each of the biochips.

At present, no practical approach is known for determining if a probe biopolymer has been accurately hybridized to a sample biopolymer of interest, and accordingly, there is a need for such a method.

SUMMARY OF THE INVENTION

The present invention is devised to satisfy such a need. Accordingly, it is an object of the present invention to provide a method for displaying information concerning the accuracy of hybridization experiments using biochips in a manner that is visually easy to understand.

In one embodiment of the present invention, a similarity score is calculated from the base sequences of subject probe biopolymers. The calculated score is represented by, for example, square patterns (i.e., similarity patterns) having varying depths in a color. The similarity pattern, probe biopolymer data and the hybridization-level data are displayed side by side so that they can be compared with each other. The comparison makes it possible to visually confirm whether a probe biopolymer with a similar base sequence to that of an object probe biopolymer has a similar hybridization level. As a result, it can be easily known whether an unexpected hybridization reaction has taken place. Also, by simultaneously displaying the hybridization-level information of the subject probe biopolymers for multiple biochips, it is possible to determine if there is any biochip with improper hybridization. The similarity pattern can be presented in a matrix-like form by arranging the subject probe biopolymers vertically and horizontally (i.e., similarity pattern matrix). This makes the displayed image more intuitive.

Further, the results of cluster analyses performed on multiple biochips and the similarity pattern matrix may be arranged side by side to make it possible to determine whether the clusters have been separated based on the biological properties, rather than physical properties, of the base sequences.

Accordingly, the present invention provides a method for displaying the results of a hybridization experiment in which a plurality of probe biopolymers immobilized on a biochip are hybridized to a sample biopolymer. The method is characterized in that the information obtained in the hybridization experiment about the hybridization level on each of the probe biopolymers is displayed together with a similarity score representing the similarity of base sequences between each of the probe biopolymers.

Also, different depths of a color may be assigned to different values of the similarity score for the purpose of displaying. Alternatively, different depths of a color may be assigned to different values of the similarity score, and subject probe biopolymers are further arranged horizontally and vertically to form a matrix for the purpose of displaying.

The information about the hybridization level may be displayed by assigning different depths of a color to different values of the hybridization level, or by providing spot images of respective probe biopolymers.

In an effective displaying method in accordance with the present invention, probe biopolymer data (e.g., name, definitions, or the like), hybridization levels and similarity scores are displayed side by side by sorting them based on the values of the similarity score between specific one of the probe biopolymers and each of the probe biopolymers. It is also effective to display the hybridization levels obtained from a plurality of biochips side by side.

Further, the profile of the changes in the hybridization levels of the subject probe biopolymers on said plurality of biochips may be statistically analyzed (e.g. by using cluster analyses), and the results of the analysis are displayed together with the results of clustering the probe biopolymers side by side.

The similarity scores are calculated from the base sequence information of the subject probe biopolymers, and square patterns each provided with a different depth in a color are assigned to the calculated similarity scores. The similarity scores are calculated for all of the possible combinations of the subject probe biopolymers, and corresponding squares are arranged in a matrix-like manner to serve as a similarity score matrix, which is displayed with the hybridization-level information for each of the subject probes so that the matrix and the hybridization information are arranged side by side. The matrix and the hybridization-level information are displayed in the order given by the sorting by the similarity scores between an object probe biopolymer and each of the other probe biopolymers. As a result, the matrix and the hybridization-level information are sorted in the order of decreasing similarity with respect to the object probe. Thus, it is possible to determine if unintended hybridization has occurred by observing the hybridization-level information in the proximity of the objective probe. Also, by selecting the information to be displayed with the similarity score matrix, the verification of the accuracy of the hybridization is possible in wider ranges.

BRIEF DESCRIPTION OF THE DRAWINGS

These as well as other features of the present invention will become more apparent upon reference to the drawings in which:

FIG. 4 is a diagram showing an example of biochip data stored in a biochip table;

FIG. 5 is a diagram showing an example of a DNA probe data stored in a DNA probe table;

FIG. 6 is a diagram showing an example of hybridization-level data stored in a hybridization-level table;

FIG. 7 is a diagram showing an example of calculated similarity scores;

FIG. 8 is a descriptive illustration of a similarity pattern;

FIG. 9 is a diagram showing an example of how a similarity pattern is generated;

FIG. 10 is a descriptive illustration of a similarity pattern matrix;

DETAILED DESCRIPTION OF THE PREFERRED EMBODIMENTS

The preferred embodiments of the present invention will now be described with reference to the accompanying drawings. While the present invention is described by means of exemplary examples, in which probe biopolymers and sample biopolymers are both DNA, it will be appreciated that the present invention is not limited to hybridization experiments where DNA probes are hybridized to sample DNA but is also generally applicable to hybridization experiments which employ combinations of other biopolymers such as hybridization between DNA probes and sample DNA binding proteins, or hybridization between monoclonal antibodies and sample proteins.

Figure 1:
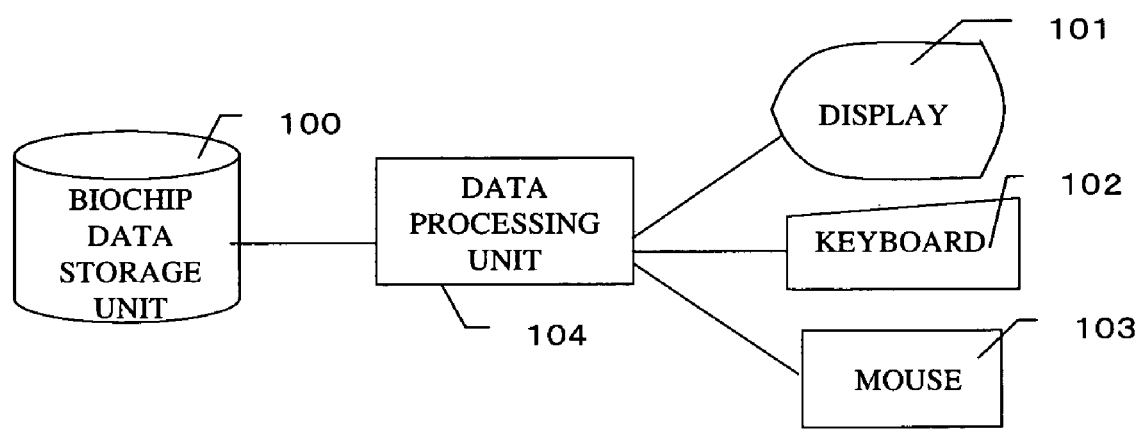
FIG. 1 is an illustration schematically showing an arrangement of a system in accordance with the present invention.

FIG. 1 shows a schematic diagram of a system in accordance with the present invention. The system includes a biochip data storage unit 100 for storing biochip data (name, definition information, experiment information or the like), data concerning levels of hybridization for each DNA probe on a biochip (levels of hybridization, spot images or the like), information concerning DNA probes (name, definition information, DNA sequences or the like) and other biochip data, a display 101 for visualizing and displaying the stored data, a keyboard 102 for entering values into the system or performing selection, an input device 103 such as a mouse, and data processing unit 104 for processing data, the processing including calculating the similarity scores of DNA sequences, generating or sorting the similarity patterns.

Figure 2:
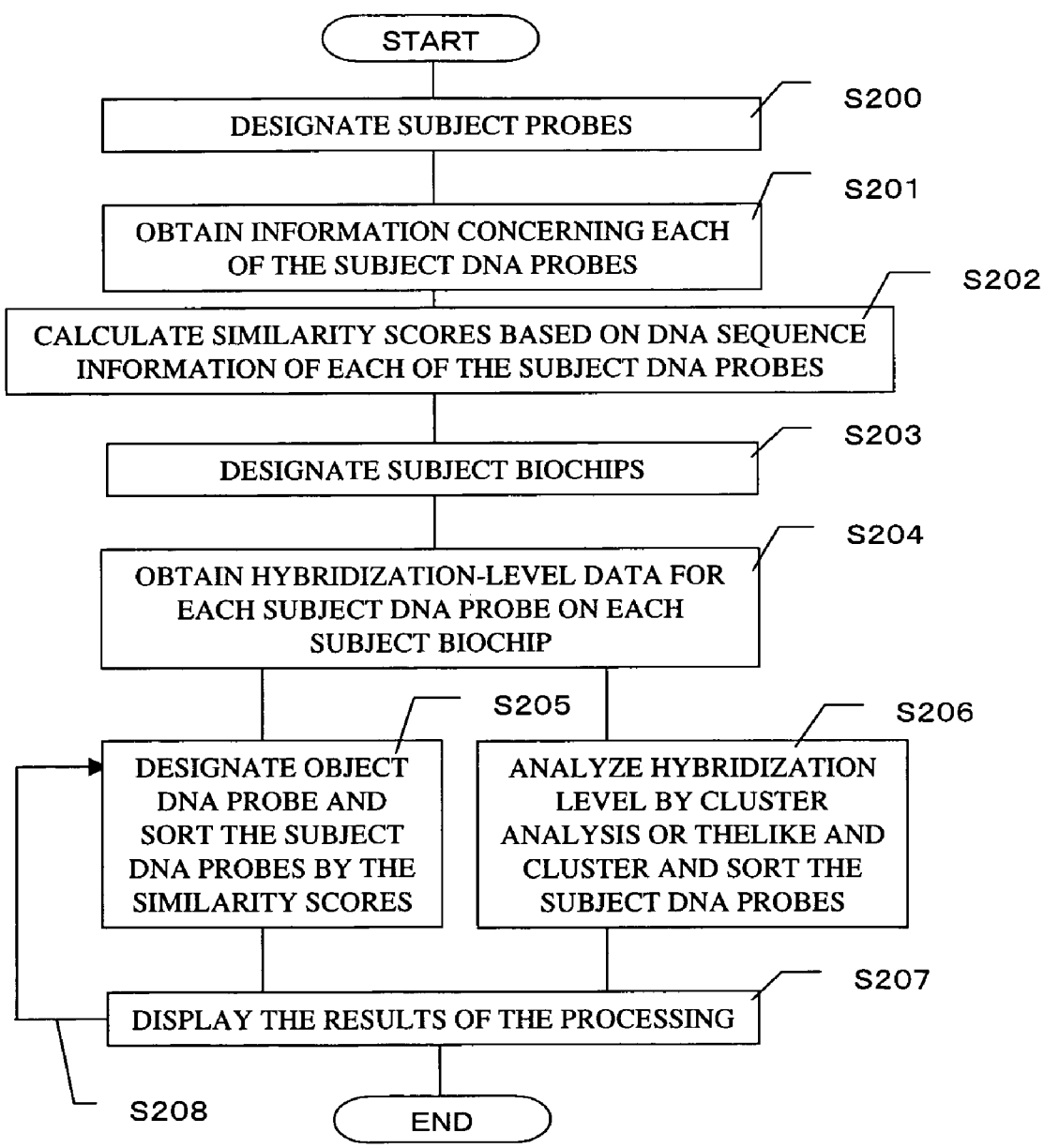
FIG. 2 is a flow chart schematically showing a flow of processes in one embodiment of the displayed image of the sequence similarity patterns in accordance with the present invention.

FIG. 2 is a flow chart schematically illustrating one example of a process for displaying a similarity pattern in accordance with the present invention. The process is described step-by-step with reference to the flow chart.

First, in step 200, a plurality of DNA probes to be investigated are designated (subject DNA probes). In step 201, information is obtained concerning each of the subject DNA probes. This means that DNA probe data (e.g., names of the DNA probes, probe definition information, and DNA probe sequences) is retrieved from the biochip data storage unit 100 for each of the subject DNA probes selected in step 200. Next, in step 202, the similarity scores are calculated between two DNA probes of the subject DNA probes for all of possible combinations. The similarity scores are calculated between the same DNA probes, as well as between two different DNA probes.

Next, in step 203, biochips to be investigated are designated (subject biochips). A single or multiple subject biochip(s) may be selected. In step 204, data is obtained concerning levels of hybridization for each subject DNA probe on each of the subject biochips. This means that data is obtained concerning levels of hybridization for a subject DNA probe on a subject biochip from the subject DNA probes selected in step 200 and the subject biochips selected in step 203.

Next, in step 205, a single DNA probe to be of concern in the investigation is selected (object DNA probe), and the subject DNA probes are sorted based on the similarity scores between the subject DNA probes and the object DNA probe. Alternatively, the process may proceed to step 206 in which data concerning levels of hybridization for a subject DNA probe on a subject biochip is processed by means of, for example, cluster analysis, and the subject DNA probes are clustered and sorted. Finally, in step 207, the results of the above processing are displayed for each of the subject DNA probes in the order obtained from the sorting in steps 205 or 206. If step 206 is taken, then additional information resulting from the data-processing, if any, is also displayed.

Processing performed in each of the steps shown in FIG. 2 will now be described in detail by means of examples as shown in FIGS. 3 through 18.

Figure 3:
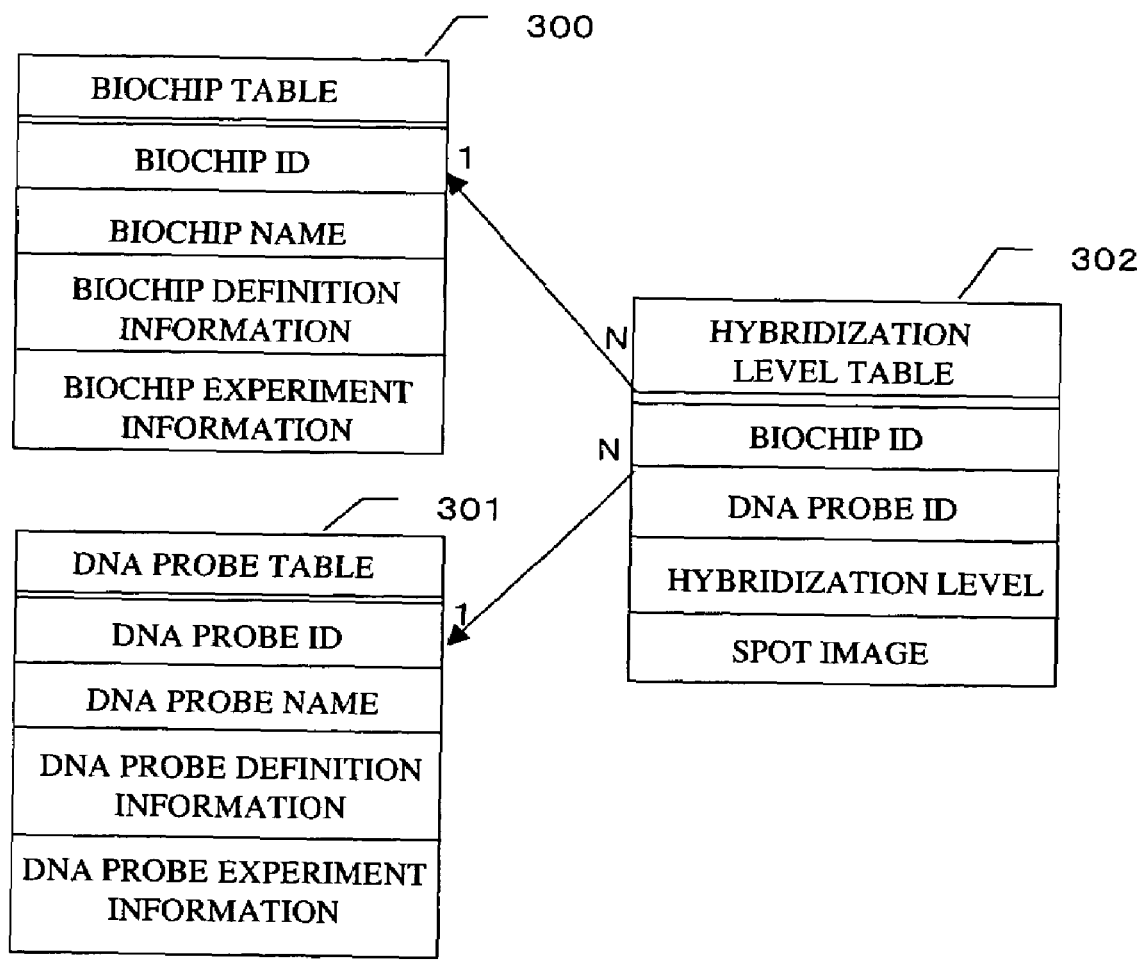
FIG. 3 is a diagram showing an example of a data structure stored in a biochip data storage unit.

FIG. 3 schematically shows an example of data structure stored in a biochip data storage unit 100. Biochip IDs, biochip names, biochip definition information and biochip experiment information are stored in a biochip table 300. DNA probe IDs, DNA probe names, DNA probe definition information and DNA probe sequences are stored in a DNA probe table 301. Also, biochip IDs, DNA probe IDs, levels of hybridization and spot images are stored in a hybridization-level table 302.

FIGS. 4, 5 and 6 show examples of biochip data stored in the biochip table 300, DNA probe data stored in the DNA probe table 301, and hybridization-level data stored in the hybridization-level table 302, respectively.

In step 200 in FIG. 2, subject DNA probes are selected from the DNA probe data table 301 stored in the biochip data storage unit 100. As an example, a case in which DNA probes designated by DNA probe IDs 1 to 5 are selected from the DNA probe data table 301 to serve as the subject DNA probes is described. In step 201, DNA probe data (e.g., DNA probe name, DNA probe definition information, and DNA probe sequences) are retrieved from the DNA probe data table 301 for each of the DNA probes selected in step 200 and designated by the DNA probe IDs 1 to 5.

FIG. 7 shows an example of similarity scores calculated in step 202. Homology scores (i.e., similarity scores) are determined according to the Smith-Waterman method using the DNA sequences of the DNA probes designated by the DNA probe IDs 1 to 5 that are retrieved in step 201. As shown, the similarity scores are displayed in a matrix-like form.

In step 203, subject biochips are selected from the biochip data table 300 shown in FIG. 4. For example, the biochip designated by the biochip ID 1 may be selected from the biochip data table 300 to serve as a subject biochip, or the biochips designated by the biochip IDs 1 to 3 may be selected to serve as subject biochips. In step 204, for example, data records are selected from the hybridization-level data 302a, 302b, . . . , based on DNA prove IDs of the subject DNA probes and biochip IDs of the subject biochips. Hybridization-level data (e.g., hybridization level and spot images) are then retrieved for each record.

The similarity scores calculated in step 202 are displayed in square patterns (similarity patterns) in which, for example, different depths in a color are assigned to different values of the similarity score. As shown in FIG. 8, a color gradient 603 is provided that corresponds to values ranging from a minimum value 602 to a maximum value 601 of the calculated similarity score. The color depths corresponding to similarity scores are determined and converted to a similarity pattern 604.

Specifically, as shown in FIG. 9, similarity scores 605 obtained for DNA probes of DNA probe IDs:1 to 5 in DNA probe data table 301 with respect to the DNA probe of DNA probe ID:1 are converted to form a similarity pattern 606. The similarity patterns may be displayed as a similarity pattern matrix by arranging them in a matrix-like form as in the example of similarity score calculation shown in FIG. 7. FIG. 10 shows an example of the similarity pattern matrix.

Figure 11:
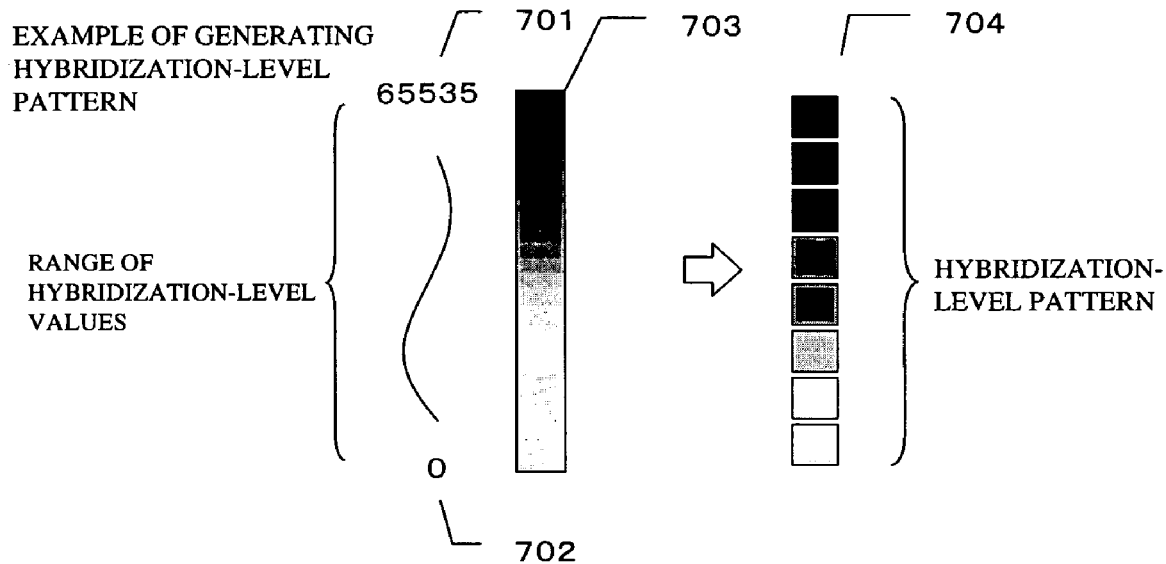
FIG. 11 is a diagram showing an example of how a hybridization-level pattern is generated.

The hybridization levels obtained in step 204 are displayed in square patterns (hybridization-level patterns) in which, for example, different depths in a color are assigned to different values of the hybridization level. As shown in FIG. 11, a color gradient 703 is provided that corresponds to values ranging from a minimum value 702 to a maximum value 701 of the hybridization level. The color depths corresponding to values of hybridization level are determined and converted to a hybridization level pattern 704.

Figure 12:
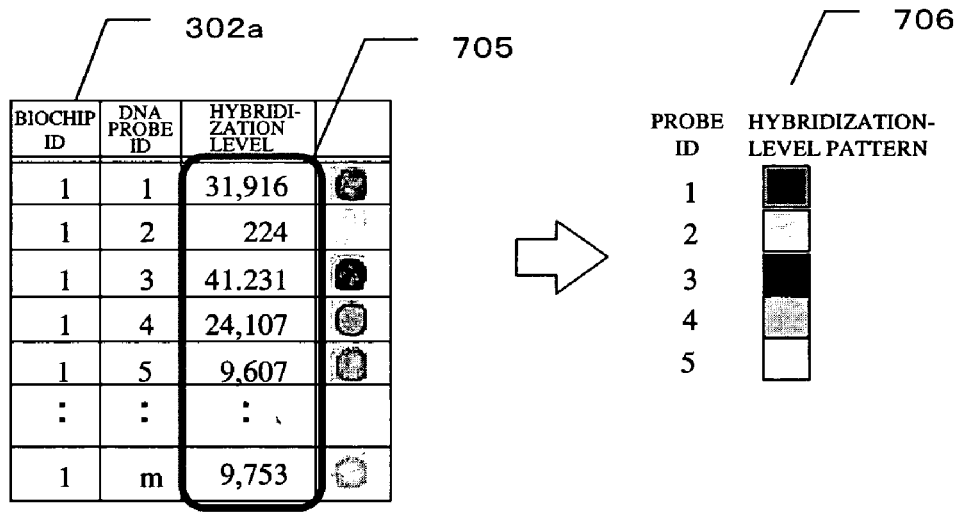
FIG. 12 is a diagram showing an example of the conversion of a hybridization-level pattern.

For example, as shown in FIG. 12, hybridization levels 705 obtained for DNA probe IDs: 1 to 5 in the hybridization-level data 302a shown in FIG. 6 are converted to form a hybridization-level pattern 706. In this example, since the value range measurable by a typical biochip measurement device is in the order of two bytes, the minimum and maximum values 702 and 701 are set to 0 and 65535, respectively, so that the values can be expressed in the measurable range. However, it will be appreciated that, in practice, a hybridization pattern by which differences in values can be made visually more distinctive can be generated by employing the range of hybridization level to be processed.

FIGS. 13 to 18 show examples of how the results of the process can be displayed. In the following examples, data is presented in a line for each of the subject DNA probes, making it easy to look at the information through the subject DNA probes. Data to be presented for each of the subject probes include DNA probe data 806, hybridization-level data 807 and a similarity pattern 808.

Figure 13:
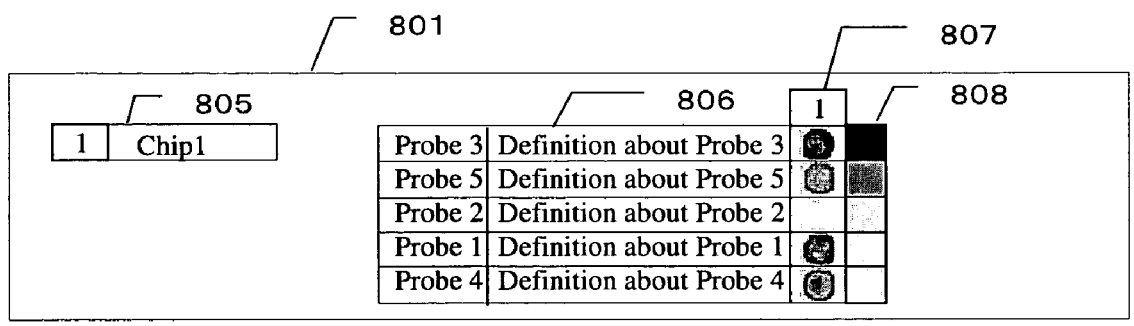
FIG. 13 is a diagram showing an example of how a similarity pattern is displayed.

FIG. 13 shows an example of a displayed data image in which Probe 3 in the DNA probe data table 301 in FIG. 5 is used as an object DNA probe. In a displayed image 801, DNA probe data 806, which includes DNA probe names and DNA probe definition information, and hybridization-level data 807, which comprises spot images on a single subject biochip, are arranged adjacent to a similarity pattern 808, which has resulted from the conversion of similarity scores with respect to the object DNA probe. The name of the subject biochip for the hybridization-level data 807 is shown in a separate window 805. It can be seen from the displayed image 801 that Probe 5 has a higher similarity to Probe 3 (objective probe) than do the other subject probes and that the hybridization level of Probe 5 is lower than that of Probe 1. This indicates that it is unlikely that the sample DNA corresponding to Probe 3 (objective probe) has been miss-hybridized to the other subjective probes including Probe 5.

Figure 14:
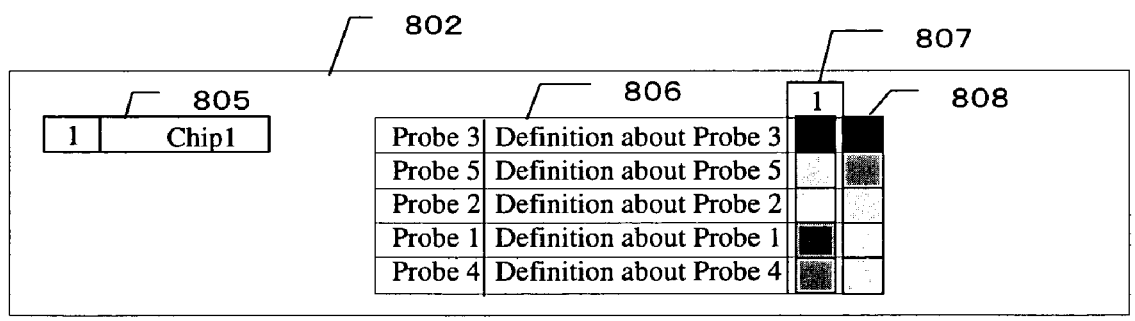
FIG. 14 is a diagram showing another example of how a similarity pattern is displayed.

FIG. 14 is a variation of the displayed image shown in FIG. 13. In a displayed image 802, DNA probe data 806, which includes DNA probe names and DNA probe definition information, and hybridization-level data 807, which comprises a hybridization level pattern on a single subject biochip, are arranged adjacent to a similarity pattern 808, which has resulted from the conversion of similarity scores with respect to the object DNA probe. The name of the subject biochip for the hybridization-level data 807 is shown in a separate window 805.

Figure 15:
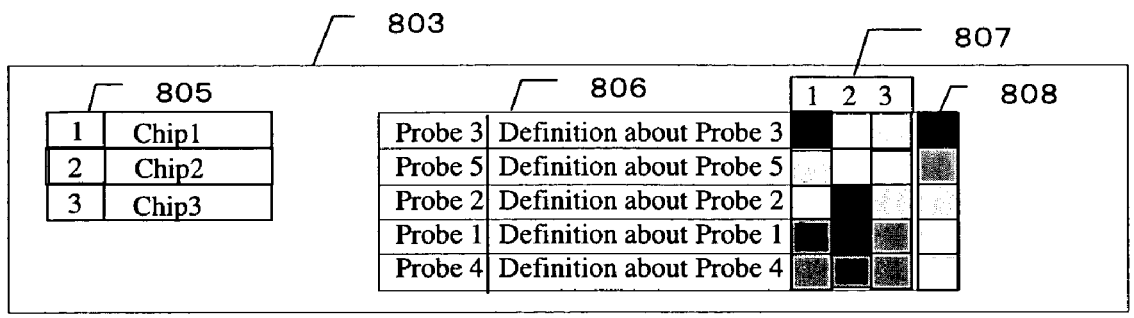
FIG. 15 is a diagram showing another example of how a similarity pattern is displayed.

Similarly, FIG. 15 shows another example of displayed data image in which Probe 3 in the DNA probe data table 301 in FIG. 5 is used as an object DNA probe. In a displayed image 803, DNA probe data 806, which includes DNA probe names and DNA probe definition information, and hybridization-level data 807, which comprises hybridization level patterns on a plurality of subject biochips, are arranged adjacent to a similarity pattern 808, which has resulted from the conversion of similarity scores with respect to the object DNA probe. The names of the subject biochips for the hybridization-level data 807 are shown in a separate window 805.

Figure 16:
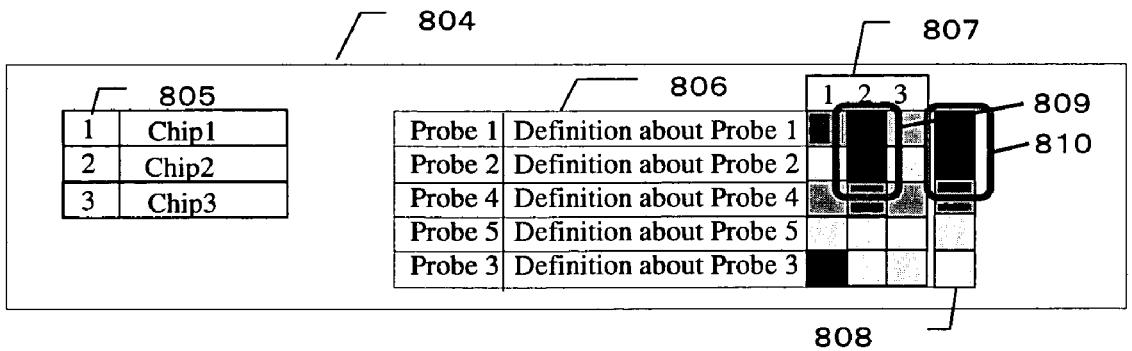
FIG. 16 is a diagram showing yet another example of how a similarity pattern is displayed.

FIG. 16 shows an example of a displayed data image in which the DNA probe with the DNA probe ID: 1(probe name: Probe 1) in the DNA probe data table 301 prepared in FIG. 5 is used as an object DNA probe. The names of the subject biochips for the hybridization-level data 807 are shown in a separate window 805. A framed portion 809 in the hybridization-level data 807 indicates that the hybridization level of Probe 1 is very close to that of Probe 2 in Chip 2. A framed portion 810 in the similarity pattern 808 indicates that the sequences of the DNA probes, Probe 1 and Probe 2, are very similar to one another. Together, these portions suggest the possibility of miss-hybridization in a readily recognizable manner.

Figure 17:
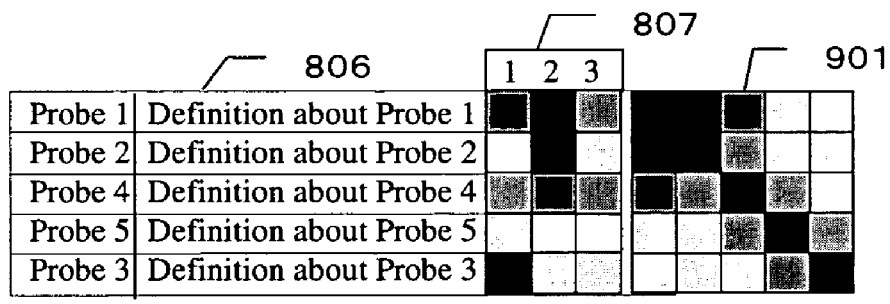
FIG. 17 is a diagram showing an example of how a similarity pattern matrix is displayed.

FIG. 17 shows an example of a displayed data image using a similarity pattern matrix. DNA probe data 806 including DNA probe names and DNA probe definition information, as well as hybridization-level data 807 comprising hybridization level patterns on a plurality of subject biochips, are displayed. In addition, a similarity pattern matrix 901 is arranged adjacent thereto in which similarity patterns are presented for all of the possible combinations between the subject DNA probes in a matrix-like manner. The names of the subject biochips for the hybridization-level data 807 are shown in a separate window 805. In this manner of displaying the image, the relationships can apparently be seen between the DNA probes with similar DNA sequences throughout the entire subject DNA probes, with respect to the hybridization-level data, for all of the DNA probes including the object DNA probe.

Figure 18:
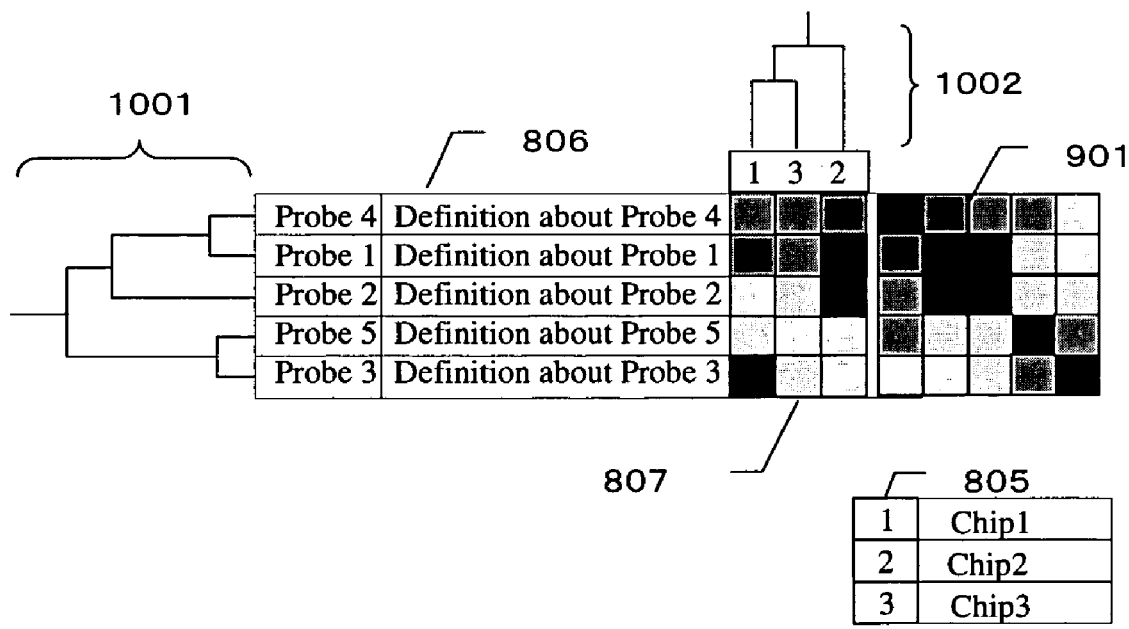
FIG. 18 is a diagram showing a similarity pattern matrix shown together with the results of cluster analysis.

FIG. 18 shows an example of a displayed data image in which a similarity pattern matrix is presented in combination with the results of the cluster analyses. In step 206 in FIG. 2, DNA probes are clustered with respect to the changes in the hybridization level on each biochip, based on hybridization level of the subject DNA probes on a subject biochip. Likewise, biochips are clustered with respect to the changes in the hybridization level for each DNA probe. The results are shown as tree diagrams 1001, 1002, respectively.

As shown, the subject DNA probes are sorted based on the results of the clustering with respect to the DNA probes. For each subject DNA probe, DNA probe data 806, which includes a DNA probe name and DNA probe definition information, and hybridization-level data 807, which comprises hybridization level patterns on a plurality of subject biochips, are displayed. In addition, a similarity pattern matrix 901 is arranged adjacent thereto in which similarity patterns are presented for all of the possible combinations between the subject DNA probes in a matrix-like manner. The names of the subject biochips for the hybridization-level data 807 are shown in a separate window 805.

In this manner of displaying the image, it is known for all of the subject biochips whether the results of the data analysis of the hybridization-level data reflect the physical properties of the DNA probe (i.e., DNA sequence of the DNA probe) due to miss-hybridization or the biological properties of the sample (the manner in which the DNA sequences are present in the sample). In the example shown in FIG. 18, it can be seen from the similarity pattern matrix 901 that Probe 1 and Probe 2 have DNA sequences that are very similar to one another while the tree diagram 1001 indicates that the probes have rather different properties from one another (Probe 1 is more closely related to Probe 4). This suggests that the results of the analyses are reflecting the biological properties, rather than the physical properties, of the DNA probes.

As described above, the data images can be displayed in the manners shown in FIGS. 13 to 18 by following the flow of the processes shown in FIG. 2. Also, after the results of the processing have been displayed, the object DNA probe may be replaced in step 208, and the data images are displayed in the same manner for the different object DNA probe. This makes it possible to verify the accuracy of hybridization.

Accordingly, the present invention provides a convenient display method which allows for the verification of the accuracy of hybridization experiments in the art of biochips by making use of DNA sequences of the subject DNA probes.

While there has been described what are at present considered to be preferred embodiments of the present invention, it will be understood that various modifications may be made thereto, and it is intended that the appended claims cover all such modifications as fall within the true spirit and scope of the invention.

What is claimed is:

1. A method for displaying results of a hybridization experiment in which a plurality of probe biopolymers immobilized on a biochip are hybridized to a sample biopolymer, the method comprising the steps of:
provingdinthe biochip immobilized with said plurality of probe biopolymers;
conducting the hybridization experiment on the provided biochip thereby hybridizing said sample biopolymer with said plurality of probe biopolymers;
determining information obtained in the conducted hybridization experiment about a hybridization level for each of the probe biopolymers;
determining a probe homologous similarity score, which represents a homologous similarity between first probe data on a base sequence of at least one of the probe biopolymers immobilized on the provided biochip and second probe data on a base sequence of at least one other of the probe biopolymers immobilized on the provided biochip, according to an algorithm for calculating degrees of homology between two biopolymer sequences; and
displaying said information about the hybridization level for each of the probe biopolymers immobilized on the provided biochip together with said probe homologous similarity score, including generating a visual graphical representation of the determined hybridization level and correspondingly determined probe homologous similarity score so as to provide at least one of a visual confirmation of similarities between the base sequences of corresponding probe biopolymers immobilized on the provided biochip used in the hybridization experiment and a visual indication of unexpected or improper hybridization.

2. The method for displaying results of a hybridization experiment according to claim 1, wherein said step of generating the visual graphical representation includes assigning different depths in a color to different values of the probe homologous similarity score.

3. The method for displaying results of a hybridization experiment according to claim 1, wherein said step of generating the visual graphical representation includes assigning different depths in a color to different values of the probe homologous similarity score, and arranging subject probe biopolymers horizontally and vertically to form a matrix.

4. The method for displaying results of a hybridization experiment according to any one of claims 1 to 3, wherein said step of generating the visual graphical representation includes displaying the information about the hybridization level by assigning different depths in a color to different values of the hybridization level, or by providing spot images of respective probe biopolymers.

5. The method for displaying results of a hybridization experiment according to any one of claims 1 to 3, wherein probe biopolymer data, hybridization levels and probe homologous similarity scores are displayed side by side by sorting them by values of the probe homologous similarity score between specific one of the probe biopolymers and each of the probe biopolymers.

6. The method for displaying results of a hybridization experiment according to claim 5, wherein the hybridization levels obtained from a plurality of biochips are displayed side by side.

7. The method for displaying results of a hybridization experiment according to claim 6, wherein a profile of changes in the hybridization level of the subject biopolymers on said plurality of biochips is statistically analyzed, and the results of the analysis are displayed together with the results of clustering the probe biopolymers side by side.

8. The method for displaying results of a hybridization experiment according to claim 1, wherein the probe data on the base sequences of the probe biopolymers for determining the probe homologous similarity score includes at least one of DNA probe names, DNA probe definition information and DNA probe sequences.

9. The method for displaying results of a hybridization experiment according to claim 1, wherein said algorithm is a Smith-Waterman method or a BLAST method.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 1 acgggacgttccctcggagg                                                    20

<210> SEQ ID NO 2
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 2 acgggacgttcccccggagg                                                    20

<210> SEQ ID NO 3
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 3 tttggacgttccaatagagg                                                    20

<210> SEQ ID NO 4
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 4 tttggacgttccaatagggg                                                    20

<210> SEQ ID NO 5
<211> LENGTH: 20
<212> TYPE: DNA
<213> ORGANISM: Artificial Sequence
<220> FEATURE:
<223> OTHER INFORMATION: DNA primer used for forming an extended
      complementary strand

<400> SEQUENCE: 5 ttgggacgttccaataggag                                                    20

<210> SEQ ID NO 6
<211> LENGTH: 20
<212> TYPE: DNA
<213> ORGANISM: Artificial Sequence
<220> FEATURE:
<223> OTHER INFORMATION: DDNA primer used for forming an extended
      complementary strand -continued

<400> SEQUENCE: 6 ttgggacgttccaataggag                                                                                          20